United States Patent
Häubl et al.

(10) Patent No.: US 10,093,790 B2
(45) Date of Patent: Oct. 9, 2018

(54) THREE-DIMENSIONAL CELLULOSE MOLDED BODY, METHOD FOR THE PRODUCTION THEREOF AND USE OF THE SAME

(71) Applicant: LENZING AG, Lenzing (AT)

(72) Inventors: Martin Häubl, Linz (AT); Josef Innerlohinger, Berg im Attergau (AT); Christian Schirk, Gmunden (AT)

(73) Assignee: Lenzing Aktiengesellschaft, Lenzing (AT)

( * ) Notice: Subject to any disclaimer, the term of this patent is extended or adjusted under 35 U.S.C. 154(b) by 0 days.

(21) Appl. No.: 15/027,923

(22) PCT Filed: Nov. 14, 2014

(86) PCT No.: PCT/AT2014/000202
§ 371 (c)(1),
(2) Date: Apr. 7, 2016

(87) PCT Pub. No.: WO2015/054711
PCT Pub. Date: Apr. 23, 2015

(65) Prior Publication Data
US 2016/0257806 A1 Sep. 8, 2016

(30) Foreign Application Priority Data
Oct. 15, 2013 (AT) ..................... 794/2013

(51) Int. Cl.
C08L 1/02 (2006.01)
C08K 3/22 (2006.01)
C08B 15/02 (2006.01)
A61K 8/02 (2006.01)
A61K 8/73 (2006.01)
A61K 31/167 (2006.01)
A61K 9/16 (2006.01)
A61Q 19/00 (2006.01)
C08J 3/12 (2006.01)

(52) U.S. Cl.
CPC .............. *C08L 1/02* (2013.01); *A61K 8/0279* (2013.01); *A61K 8/731* (2013.01); *A61K 9/1652* (2013.01); *A61K 9/1682* (2013.01); *A61K 31/167* (2013.01); *A61Q 19/00* (2013.01); *C08B 15/02* (2013.01); *C08J 3/126* (2013.01); *C08K 3/22* (2013.01); *A61K 2800/10* (2013.01); *A61K 2800/654* (2013.01); *C08J 2301/02* (2013.01); *C08L 2205/18* (2013.01); *C08L 2207/53* (2013.01)

(58) Field of Classification Search
CPC ........ C08B 15/02; C08L 1/02; C08L 2205/18; C08L 2207/53; C08J 3/126; C08J 2301/02; C08K 3/22; A61K 8/025; A61K 31/167; A61K 9/1682; A61K 9/1652; A61K 8/731; A61K 8/0279; A61K 2800/10; A61K 2800/28; A61K 2800/654; A61Q 19/00
See application file for complete search history.

(56) References Cited

U.S. PATENT DOCUMENTS

| | | |
|---|---|---|
| 5,024,831 A | 6/1991 | Kurisaki et al. |
| 5,064,950 A | 11/1991 | Okuma et al. |
| 5,331,801 A | 7/1994 | Heifetz |
| 5,369,861 A | 12/1994 | Ball et al. |
| 5,447,603 A | 9/1995 | Michalowski et al. |
| 5,481,864 A | 1/1996 | Wright |
| 5,589,125 A | 12/1996 | Zikeli et al. |
| 5,601,767 A | 2/1997 | Firgo et al. |
| 5,609,676 A | 3/1997 | von der Eltz |
| 5,795,488 A | 8/1998 | Kalt et al. |
| 6,010,594 A | 1/2000 | Henricson et al. |
| 6,183,865 B1 | 2/2001 | Yabuki et al. |
| 6,527,987 B1 | 3/2003 | Yabuki et al. |
| 9,133,570 B2 | 9/2015 | Lightman |
| 9,163,095 B2 | 10/2015 | Innerlohinger et al. |
| 2001/0050153 A1 | 12/2001 | Wajer et al. |
| 2002/0037407 A1 | 3/2002 | Luo et al. |
| 2002/0081428 A1 | 6/2002 | Luo et al. |
| 2002/0124366 A1 | 9/2002 | Hirsch |
| 2002/0189035 A1* | 12/2002 | Ruf .......................... C08J 5/18 8/536 |

(Continued)

FOREIGN PATENT DOCUMENTS

| | | |
|---|---|---|
| AT | 287 905 B | 2/1971 |
| AT | 101 779 B | 11/1996 |

(Continued)

OTHER PUBLICATIONS

Abu-Rous et al. (Visualisation of the Nano-Structure of Tencel® (Lyocell) and Other Cellulosics As an Approach to Explaining Functional and Wellness Properties in Textiles in Lenzinger Berichfe, 85 (2006), 31-37).*

Gericke et al. ("Functional Cellulose Beads: Preparation, Characterization, and Applications," in Chemical Reviews, Mar. 2013), pp. 4812-4836.*

M. Abu-Rous et al., "Visualisation of the Nano-Structure of Tencel® (Lyocell) and Other Cellulosic as an Approach to Explaining Functional and Wellness Properties in Textiles", Lenzinger Berichte 85 (2006), pp. 31-37.

(Continued)

*Primary Examiner* — Blessing M Fubara
(74) *Attorney, Agent, or Firm* — Fitzpatrick, Cella, Harper & Scinto

(57) ABSTRACT

The present invention relates to a three-dimensional cellulosic molded body that has an optically detectable core/shell structure, the shell having a higher density and a lower crystallinity than the core, and the core having a sponge-like structure. The invention further relates to a method for producing this molded body as well as to its use, especially in the cosmetics and pharmaceutical industries.

25 Claims, 4 Drawing Sheets

(56) References Cited

U.S. PATENT DOCUMENTS

| | | | |
|---|---|---|---|
| 2003/0138473 A1* | 7/2003 | Koblish | A61B 17/866 424/423 |
| 2004/0131690 A1 | 7/2004 | Lynch | |
| 2006/0144534 A1 | 7/2006 | Paren et al. | |
| 2007/0249774 A1 | 10/2007 | Guzauskas | |
| 2010/0139875 A1 | 6/2010 | Paren et al. | |
| 2010/0209708 A1 | 8/2010 | Braun et al. | |
| 2010/0297445 A1 | 11/2010 | Guentherberg et al. | |
| 2014/0041821 A1 | 2/2014 | Graveson et al. | |
| 2014/0182801 A1 | 7/2014 | Hawkins et al. | |
| 2015/0136346 A1 | 5/2015 | Bogren et al. | |
| 2015/0291762 A1 | 10/2015 | Watanabe et al. | |
| 2016/0237619 A1 | 8/2016 | Weilach et al. | |
| 2016/0326671 A1 | 11/2016 | Schrempf et al. | |
| 2016/0369456 A1 | 12/2016 | Flynn et al. | |

FOREIGN PATENT DOCUMENTS

| | | |
|---|---|---|
| AT | 515152 A1 | 6/2015 |
| CN | 102199310 A | 9/2011 |
| CN | 102660791 A | 9/2012 |
| CN | 102677230 A | 9/2012 |
| EP | 0 356 419 B1 | 12/1992 |
| EP | 0 584 318 B1 | 5/1996 |
| EP | 0 781 356 B1 | 7/1998 |
| EP | 0 717 131 B1 | 11/1998 |
| EP | 0 671 492 B1 | 9/1999 |
| EP | 2 589 689 A2 | 5/2013 |
| GB | 685843 A | 1/1953 |
| JP | 08239504 A | 9/1996 |
| WO | 02/057319 A2 | 7/2002 |
| WO | 2004/043329 A2 | 5/2004 |
| WO | 2009/036480 A1 | 3/2009 |
| WO | 2009/037146 A1 | 3/2009 |
| WO | 2009/065891 A1 | 5/2009 |
| WO | 2010/071910 A2 | 7/2010 |
| WO | 2011/077446 A1 | 6/2011 |
| WO | 2011/130276 A2 | 10/2011 |
| WO | 2013/006876 A1 | 1/2013 |
| WO | 2015/077807 A1 | 6/2015 |

OTHER PUBLICATIONS

Gericke et al., "Functional Cellulose Beads: Preparation, Characterization, and Applications", Chemical Reviews, 113, (2013) pp. 4812-4836.

Trygg et al., "Physicochemical Design of the Morphology and Ultrastructure of Cellulose Beads", vol. 93, Issue 1, (2013) pp. 294-299.

M. Opietnik et al., "Tencel® Gel—A Novel Cellulose Micro Suspension", Lenzinger Berichte 91 (2013), pp. 89-92.

L. Youhanan, "Enviommental Assessment of Textile Material Recovery Technique: Examining Textile Flow in Sweden", (2013) p. 18-19.

International Preliminary Report on Patentability and Written Opinion of the International Searching Authority issued in International Application No. PCT/AT2014/000202 (9 pages).

International Preliminary Report on Patentability and Written Opinion of the International Searching Authority issued in International Application No. PCT/AT2014/000203 (6 pages).

Written Opinion of the International Searching Authority issued in International Application No. PCT/AT2014/000205 (5 pages).

International Search Report for PCT/AT2014/000202 dated May 12, 2015.

International Search Report for PCT/AT2014/000203 dated May 21, 2015.

International Search Report for PCT/AT2014/000205 dated Mar. 10, 2015.

Pending U.S. Appl. No. 15/027,937, filed Apr. 7, 2016 (drawings attached).

Pending U.S. Appl. No. 15/027,945, filed Apr. 7, 2016 (drawings attached).

Zhang, et al., "Structure and Properties of Regenerated Cellulose Films Prepared from Cotton Linters in NaOH/Urea Aqueous Solution," Ind. Eng. Che. Res., 40, pp. 5923-5928 (2001).

Röder et al., "Comparative Characterisation of Man-Made Regenerated Cellulose Fibres," Lenzinger Berichte, 87, pp. 98-105 (2009).

Björquyist et al., "Textile qualities of regenerated cellulose fibers from cotton waste pulp," Textile Research Journal pp. 1-8 (2017).

* cited by examiner

THREE-DIMENSIONAL CELLULOSE MOLDED BODY, METHOD FOR THE PRODUCTION THEREOF AND USE OF THE SAME

BACKGROUND OF THE INVENTION

Field of the Invention

The present invention describes a novel type of cellulose II particles as well as suitable production methods. The properties of these particles make them particularly suited for use in cosmetic and pharmaceutical applications. The particles are characterized by a sponge-like microstructure in their interior, surrounded by a compact outer shell.

Description of Related Art

Cellulose powders and other systems that contain particulate cellulose have long been known, and there have also been an increasing number of new developments in this field, especially in recent years. The most widely used are dry fibrous powders that are obtained by comminuting pulp by means of suitable units. Depending on the pulp and the type of processing (comminution including possible modifications) employed, different qualities can be produced. In this context, it can also be considered as a variant to comminute plants (plant parts) directly, rather than pulp. However, in that case, the obtained particles also contain, in addition to cellulose, higher percentages of other substances such as lignin or hemicelluloses and exhibit greater variations as regards homogeneity. Due to the macromolecular structure of the cellulose, all powders described so far are fibrous, i.e., the particles exhibit a pronounced L/D ratio.

Another widely used class of cellulose powders are the so-called microcrystalline celluloses (MCC). The preparation of MCC from pulp includes, in addition to mechanical comminution, a treatment with acid whereby the amorphous fractions of the cellulose are decomposed and a material having a high crystalline content is obtained. Depending on the type of procedure, the various crystallites can be brought into different shapes. Thus, apart from fibrous particles, aggregates/agglomerates of approximately spherical shape are also possible. In the case of MCC or conventional fibrous cellulose powder, the options for incorporating or applying additional materials into or onto the particles are limited. Applying additives is possible only in the form of a coating or incorporation in the aggregates or agglomerates. In this connection, a frequently employed method is granulation, where the desired final particles are composed of smaller particles. In part, also these base particles themselves were produced by previous grinding, which makes the entire process costly.

All previously described materials have the same microstructure, that is, an arrangement of the cellulose molecules, which in technical literature is referred to as a structure type—in this case, the cellulose I structure. This is the type that is formed by plants and is not altered by the processes employed in the production of the already described particles, either.

Apart from cellulose I, there also exists another frequent structure type that is referred to as cellulose II and constitutes the thermodynamically more stable form. The two structure types can be distinguished easily by radiographic methods or also by NMR. Cellulose I can be converted into cellulose II by dissolution in suitable solvents and subsequent regeneration. This process is also employed in industrially employed fiber production methods, such as for example in the viscose process and the lyocell process. Recently, there have also been a large number of publications on the topic "Ionic liquids as solvents for cellulose", in which case the implementation at industrial scale still needs to be accomplished. One advantage of all these methods is that the dissolution and subsequent regeneration of the cellulose allows for a significantly more variable shaping of the particles. Thus, it is actually possible to obtain native spherical particles without having to compose them of subunits as is the case with MCC. Another advantage is that in the course of the processes additional substances can also be incorporated directly into the particles and can, of course, also be applied to their surfaces.

Apart from these dry powders of fibrous or spherical particles, there are also suspensions of cellulosic particles, often referred to as cellulose gels. The simplest method for their preparation consists in dispersing a suitable cellulose powder in water. However, the trend is clearly toward more sophisticated methods and materials. In recent times, microscaled and nano-scaled cellulose suspensions, in particular, have been the focus of interest. They can be encountered under various designations such as microfibrillated cellulose (MFC) or nanocellulose. Again, such materials can be produced based on either cellulose I or cellulose II. In this connection, the methods for their production are mostly very costly and energy-consuming and can be applied to larger-scale environments only to a limited extent.

This basic overview already shows that a large number of cellulosic particle systems to choose from are known to those skilled in the art. As a result, also the areas of application for cellulosic particles have become numerous and range from the construction industry to reinforced plastics and through to the pharmaceutical and cosmetics industries. The known particles are able to cover many applications, which however partly entails an additional effort, as the requirements are not fully satisfied by the existing materials and additional processing steps (modifications) are necessary.

Apart from pure cellulose, several cellulose derivatives (such as methyl cellulose or carboxymethyl cellulose) are used (especially also in cosmetics) that are partly soluble in water. In addition, there exists a large number of mineral or synthetic-based particles, where especially in the case of the latter the modification options are significantly more diverse. Especially complex cosmetic products contain a large number of ingredients in order to achieve the desired effects, which obviously make their formulation a complex procedure.

US 2010/0297445 describes the production of spheres from polymers, for example, of cellulosic spheres from a cellulose solution in so-called organic solvents such as 1-ethyl-3-methyl-imidazolium acetate, by means of an underwater granulator. Subsequently, the spheres are dried by means of a solvent exchange. Nothing is disclosed about the inner structure of these spheres. Also the treatment of these spheres after their shaping, such as washing or removing of residual solvent, is not specified in detail.

WO 2009/036480 A1 discloses the production of spherical cellulose particles from a cellulose solution that is as amorphous as possible, comprising several comminuting steps. This document discloses that in the first comminuting step also an underwater granulator can be used in addition to other units. It is not disclosed which structure the resulting intermediate product has. Then, the resulting intermediate product is comminuted further in the never dried state.

WO 2009/037146 also discloses cellulose beads. They are crosslinked by various methods in order to increase their strength. Crosslinking also causes the almost total loss of the swellability of the cellulose beads.

WO 02/057319 discloses monodisperse cellulose spheres but does not offer any quantitative statements about their inner structure. These spheres are made from solutions containing no more than 10% by weight of cellulose; in the examples, however, no more than 4% by weight of cellulose are used, which suggests that the use of cellulose solutions of a higher concentration was not possible with the invention according to WO 02/057319.

US 2004/0131690 describes the production of cellulose beads for use in the cosmetics, pharmaceutical or similar industries. The cellulose beads are formed by agglomeration of microcrystalline cellulose with additional additives. Hence, the cellulose beads are not compact cellulose particles, but rather microgranules or an agglomerate. The structure of the cellulose beads is not disclosed in detail.

A review about cellulose beads can be found in "M. Gericke et al., Functional Cellulose Beads: Preparation, Characterization and Applications. Chemical Reviews 113, 2013, pp. 4512-4836". However, the production methods described are largely limited to laboratory methods. While different morphologies are mentioned, they are not described in detail, and the relationships between production and structure are only hinted at. The major part of the article deals with the further functionalization of cellulose beads.

A more detailed description of the relationships between the production of cellulose beads and their structure can be found in "J. Trygg et al., Physicochemical design of the morphology and ultrastructure of cellulose beads. Carbohydrate Polymers 93, 2013, pp. 291-299". It describes the NaOH-urea solvent system with cellulose concentrations of up to 6%. In certain conditions, core/shell structures can be created according to this document, however, with the shell mostly having a thickness of only a few μm. Only in extreme regeneration conditions (10-molar nitric acid) can the thickness of the skin be increased to 50 μm; otherwise, it can be influenced only to a small extent. A more detailed characterization of the shell (for example, as compared to the core) is not provided.

Summing up, it must be noted that, for use in the cosmetics and pharmaceutical industries, only such cellulosic particles with functional properties such as the slow, controlled release ("slow release") of active pharmaceutical or cosmetic agents, the change of the properties by external influences, for example by pressure ("stimuli response"), and ("sensoric booster") properties in oil/water emulsions were known from prior art that were produced by agglomeration of even smaller particles. Such a multi-step process is complex, as one might expect, and thus costly. For instance, the grinding step for preparing the subparticles is highly energy-consuming. On the other hand, cellulosic particles are already known in the art, which already have the particle size required for the above uses, but these particles do not have the above-mentioned functional properties.

Object

In view of this state of the art, there still exists a demand for cellulose particles having the relevant improved properties, especially in the higher-value fields of cosmetics and pharmaceuticals. The particles should already come with these properties to be begin with and not have to be provided with them later through an additional step in the production process or through the addition of further additives, as has partly been necessary up to today. In this connection, the following characteristics are of special interest: slow, controlled release—"slow release"—of active agents (pharmaceutical or cosmetic), change of the properties by external influences—"stimuli response"—(for example by pressure), improved swellability, a defined inner structure (for example a clearly defined, reproducibly producible core/shell structure), and a defined surface condition. These and possibly other functionalities need to be integrated in a defined manner during the production of the particles. In addition, the production methods need to be as simple as possible and thus easy to implement at an industrial scale. Ideally, the multifunctionality of these particles should also simplify the formulation and production of the final products, as, on the whole, a smaller number of ingredients would then be required. Another advantage could result if such novel cellulose particles were also able to replace synthetic materials. This way, it would be possible to cater to the increased demand for products made of renewable raw materials.

Now, the inventive solution to the above described object consisted in producing the cellulose particles in one step, rather than composing them of subparticles. In this connection, particular attention was paid to the selection of the relevant process parameters, as they already define the properties of the particles.

DESCRIPTION

Figure 1:
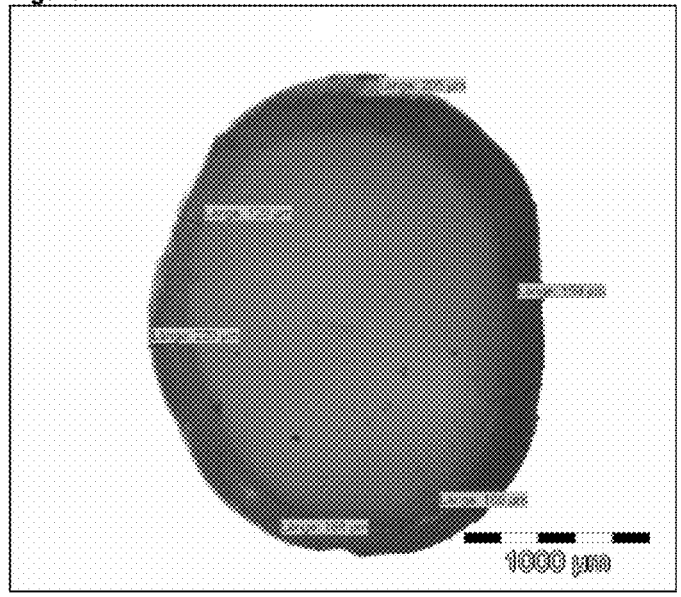
FIG. 1 depicts an optical microscope image of an exemplary cellulose bead made in accordance with the present invention.

This object was now solved by a three-dimensional cellulosic molded body that has an optically detectable core/shell structure, the shell having a higher density and a lower crystallinity than the core and the core having a sponge-like structure. As used herein, the term "optically detectable" means that the core/shell structure can be detected by means of light microscopy, X-ray spectroscopy and/or NMR spectroscopy. In this connection, microscopy is suited for both dry and swollen samples. X-ray spectroscopy, however, is limited to dry, especially air-dry, samples, and NMR spectroscopy is limited to molded bodies in the swollen state. This is due to the necessity of preparing the samples. Since the molded bodies of the invention are produced from a cellulose solution, they always have the cellulose II structure type.

Preferably, the shell of the molded body of the invention has a relative density from 65% to 85%, and the core has a relative density from 20% to 60%. Here, the relative density is related to compact cellulose.

In a preferred embodiment, the shell thickness is between 50 µm and 200 µm.

Preferably, the ratio of the shell thickness to the total diameter of the molded body is between 1:5 and 1:50.

Preferably, the molded bodies of the invention are substantially spherical, but can also be cylindrical, ellipsoidal, or ovoid. However, the ratio of the semiaxes (length:diameter) of the molded body should not exceed 3:1.

Depending on the intended use, the molded bodies of the invention can either be used dried or in the never-dried state, the never-dried variant of the cellulose beads preferably having a moisture content from 25 to 300% by weight, related to the cellulose quantity.

Depending on the intended use, the molded bodies of the invention can contain additive substances that were incorporated during their production. Preferably, these additive substances are selected from the group comprising ZnO, $TiO_2$, $CaCO_3$, $CaCl_2$, kaolin, $Fe_2O_3$, aluminum hydroxide, plastics-based color pigments, activated carbon, superabsorbent materials, phase-change materials, flame retardants, biocides, chitosan, as well as other polymers and biopolymers.

Furthermore, the molded bodies of the invention have a high water retention capacity (WRC). For example, after 2 h of swelling in deionized water, the WRC for cellulose beads dried at normal pressure is typically within the range from 70 to 90% by weight and for supercritical $CO_2$-dried or freeze-dried cellulose beads it is typically within the range from 120 to 150% by weight.

Furthermore, the present invention relates to a method for producing the above-described three-dimensional cellulosic molded body of the invention which has an optically detectable core/shell structure, characterized in that it comprises the following production steps:

a. dissolution of the cellulose according to a lyocell process in order to obtain a solution with 10 to 15% by weight of cellulose;

b. extrusion of the cellulose solution obtained in step a. without air gap directly into a precipitation bath;

c. regeneration process, where, when the cellulose solution enters the precipitation bath, the difference between the NMMO concentrations of the cellulose solution and the precipitation bath is to be 15-78% by weight, preferably 40-70% by weight, and the difference between the temperatures of the cellulose solution and the precipitation bath is to be 50-120 K, preferably 70-120 K, more preferably 80-120 K;

d. washing process according to the percolation principle, including at least one alkaline washing step, preferably at pH 9-13;

e. optionally, a drying process which does not abrasively damage the outer skin of the molded bodies;

the washing process mentioned in d.) preferably being performed in several stages and in a countercurrent configuration and containing at least one alkaline step.

Suitable dissolution processes include, for example, the viscose, the lyocell, or the cuprammonium process; it is also possible to dissolve the cellulose in NaOH or suitable ionic liquids. Generally, the invention is not limited to certain solvents or processes, but by using different methods the structure of the obtained particles can be additionally influenced. However, the lyocell process which, in principle, is known to those skilled in the art and described in EP 0356419, among others, is preferred. During the production of the spinning dope, in any event prior to the extrusion, substances can be additionally incorporated into it, as has already been described hereinabove. Based on the cellulose solution, shaping is carried out, wherein—especially in the precipitation process—care must be taken that no fibrous structures are formed. This is not a trivial requirement, as cellulose, because of its macromolecular structure, tends to form fibrous domains. This problem is solved by initially bringing the cellulose solution without any substantial shear into the desired shape and then also selecting the regeneration conditions as necessary. In this connection, it is absolutely necessary to extrude the cellulose solution directly, i.e., without an air gap, into a precipitation bath and to comminute the solution strand in a way that yields particles of substantially equal size. Suitable units for this step are, for example, underwater or strand granulators that can be used to produce not only spherical particles, but also cylinders, ellipsoids of revolution, and ovoids. The units just mentioned also meet the additional requirements for the production process. That is to say, the particles produced should be of the most uniform size possible, while the properties can be controlled via the process parameters. At the same time, the method should have a high throughput.

Granules of different sizes can be produced from lyocell spinning dope for example by using an EUP50 underwater granulator from Econ, where, depending on the configuration of the die plate and the die hole, high throughputs from 2 to 30 kg/h—calculated based on 100% cellulose final product washed free of NMMO and dried—are possible. In this process, the granules produced can be separated from the process water by using a mechanical centrifugal dryer. In other embodiments, such solid/liquid separations can be achieved, e.g., by means of hydrocyclones, pusher centrifuges, or also by screens. Granulators of various sizes are commercially available, and, due to the simplicity of the method for granulating spinning dope, scaling it up to an industrial scale is relatively easy. Accordingly, it is possible, for example, to use a single granulator of the EUP 3000 type to produce about 5000 tons of granules per year. Furthermore, significantly bigger machines from other manufacturers are also available.

In another embodiment, special lyocell dies with die hole diameters from 0.5 to 5 mm can also be used to make cellulose strands that, after passing a washing section, are fed to a strand granulator. Critical in this respect are the washing, the feeding, and the drawing-in of the various strands into the strand granulator, as the strands are very flexible. In this way, it is possible to obtain cylindrical granules.

The viscosity of the cellulose solution also has a large impact on the properties of the obtained particles, as it usually dominates the viscosity difference between the cellulose solution and the precipitation bath. Preferably, the precipitation bath is aqueous (with a viscosity of about 1 Pa·s), however, by adding thickeners (polymers), also the viscosity of the precipitation bath can be increased significantly. A smaller viscosity difference results in a thinner shell. According to the invention, the viscosity difference between the cellulose solution and the precipitation bath is at least 600 Pa·s, preferably within the range from 750 to 1200 Pa·s. (related to zero viscosity).

The thickness of the shell is influenced decisively by the difference in NMMO concentration when the cellulose solution enters the precipitation bath. The greater it is, the thicker the shell of the molded bodies produced according to the invention will be. The difference in concentration reaches its maximum if clean water is used as the precipitation bath and if the precipitation bath at the point of entry of the cellulose solution is mixed so well that any extracted NMMO will be transported away immediately.

The thickness of the shell is also influenced by the difference in temperatures when the cellulose solution enters the precipitation bath. The greater it is, the thicker the shell of the granules produced according to the invention will be.

In addition to the option of using underwater granulation in a liquid precipitation bath, there also exists the option of coagulation in a gaseous medium.

The preferred process principle for washing out the molded bodies of the invention at an industrial scale is countercurrent washing in order to keep the required washing water quantity and the costs of recovery within limits. 10 to 12 washing stages are necessary to reach the required cleanness of the molded bodies. In the event of small residual NMMO contents, it is also advantageous to increase the washing water temperature. In this case, a washing water temperature from 60° C. to 100° C. is preferred. In order to efficiently remove also small amounts of decomposition products of the solvent, an additional, alkaline step is necessary, with pH values from 9-13 being preferred for use.

In principle, the methods suited for the industrial-scale wash of the invention are particularly all types of solid/liquid extractions in continuous or batch operation. However, methods according to the percolation principle, i.e., with a crosswise countercurrent wash, are preferred. Suitable appliances for this purpose are carousel extractors or De-Smet, Crown, or Bollmann type extractors, among others. Cascades are also suited for this purpose. Such extractors are also used, for example, for maceration. In principle, pusher centrifuges would also be suited, but it is important for the method of the invention to avoid any shear or compression loading of the granules as much as possible so that centrifuges do not really qualify as suitable. Also suited are columns according to the ion exchanger principle, where the solvent for cellulose is preferably displaced in a top-to-bottom direction via the column. Again, they can be arranged into cascades.

In view of the diverse options of use of the products made according to the invention, it is important to remove the NMMO, if possible without leaving any residues, because NMMO may have an oxidizing effect on some active substances that are introduced into the products later on.

After washing the granules, the adhering excess moisture should be removed from the particles in order to minimize the drying costs and to make the granules free flowing. Suitable units for this are centrifuges and decanters as well as belt filters that can be operated continuously or in a batch mode.

Also, steam sterilization can be carried out as an additional process step after washing the granules. The steam sterilization causes the water retention capacity of the never-dried cellulose beads to decrease, and pre-dewatering prior to drying can be performed with greater efficiency.

In view of the use in the cosmetics industry, where many products are aqueous formulations or emulsions, never-dried particles having a defined moisture content constitute a preferred embodiment of this invention. This causes the very open pore structure that exists after the regeneration and washing out of the solvent to be maintained and makes the cellulose particles very receptive and accessible.

Furthermore, coagulating the spinning dope by means of the above-mentioned units causes a core/shell structure to be formed. This core/shell structure becomes manifest in the form of a compact transparent outer skin (shell) and a sponge-like white inner part (core) of the granules.

This structure is responsible for the controlled release properties of the molded bodies of the invention in the release of active cosmetic or pharmaceutical agents, as the active agents that are readily available in the sponge-like inner part must penetrate the very compact outer skin during such release. This delays the release of the active agents. The thickness and structure of this outer skin of the granules can be changed by changing the precipitation medium parameters.

Between step d. and step e., an enzymatic treatment can be carried out in order to impart the necessary functional properties to the molded body of the invention as is described in detail hereinafter. Preferably, one or several enzymes are used for this purpose, selected from the group comprising exo- and endo-1,4-b-glucanases, glucosidases, and xylanases. Surprisingly, in an enzyme treatment of the particles of the invention, not only the surface is attacked (it is smoothed), but also the porous structure in the inner part. This suggests that enzymes are able to migrate into the inner part of the particle. Thus, according to the invention, the strength of the particle can be adjusted infinitely by means of enzyme treatment. Furthermore, this shows that enzymes or proteins are able to penetrate into the inner part of the granules and that loading the thus easier accessible granules with these substances is possible. The enzyme treatment of the granules also shows that both enzymes and proteins can be received by the particles. Subjected to the necessary drying, they can also be encapsulated and immobilized, respectively.

The formation of this core/shell structure makes it possible to also produce granules having so-called stimuli response properties. Thus, it is possible, on the one hand, to significantly change the elasticity of the granules via the variable configuration of the outer skin, but it is also possible, on the other hand, to alter both the inner part of the granules and their outer skin through chemical or enzymatic modification or the variation of the precipitation medium parameters such that the granules will burst open when subjected to only little pressure between the fingers and thus will selectively release their contents (for example, form a hydrogel). The hydrogel resulting as a consequence of the granules bursting open has very interesting cosmetic properties. For example, no stickiness, greasiness, or oiliness of the hydrogel can be detected. Also, its particle size and granularity can be adjusted individually through the duration of the chemical modification, enzymatic treatment, or also the change of the precipitation parameters. Therefore, the granules can also be used as texturizers in the cosmetic industry.

This stimuli response effect is of special significance for the cosmetics and pharmaceutical industries, as active cosmetic or pharmaceutical agents, for example, but also color pigments or colors of decorative cosmetics, which were incorporated into the granules, can thus be released selectively. Furthermore, the granules can be used as a peeling or as exfoliants having a stimuli response effect. In this case, the granules can, in their inner part, contain abrasive pigments or also enzymes that can be released when the granules burst open after being rubbed on and thus achieve the desired peeling effect. The stimuli response effect of the granules can be adjusted individually through the duration of the chemical modification, the enzymatic treatment, or also through the change of the precipitation medium parameters.

If particles that have only a low moisture content are advantageous for certain applications, the particles of the invention can also be dried by means of different drying methods. In a preferred embodiment of the method according to the invention, the drying process is performed by normal-pressure drying, air stream drying, fluidized-bed drying, freeze drying, or supercritical CO2 drying. Drying is a challenge insofar as product moisture is very high. In the case of the cellulose beads, it is necessary to cope with moisture contents of 70-75% by weight, and drying must be performed down to the equilibrium moisture content of 10-13% by weight, and for some applications down to <5% by weight. According to the invention, drying should be carried out in an as contactless manner as possible in order to protect the product from damage.

Surprisingly, drying in the fluidized-bed method has proved to be particularly non-damaging and efficient. The continuous circulation and loosening of the material greatly facilitates the removal of the moisture. Furthermore, as regards abrasion, the drying process is very gentle with the product. In addition, it is possible to achieve high throughputs and short drying times. These again cause yellowing, which normally occurs due to the impact of elevated temperatures, to be extremely low. In addition, the process can be operated continuously. High bulk volumes of the material, which can partly be encountered in other drying methods, would cause the moisture to remain between the granules for a very long time, whereby the drying time would increase immensely and the long exposure to high temperatures would also entail the risk of yellowing. Here, conical dryers or crystallizers, for example, would have to be mentioned as examples. In these units, stirring imparts high shear on the product, which causes the outer skin to be abraded and a large amount of dust to be created. Furthermore, this abrasion also alters the thickness of or destroys the shell layer, which would reduce or eliminate the controlled release properties of the product. Therefore, these units are not suitable for the method according to the invention.

According to the invention, vibration dryers can still be regarded as an alternative to fluidized-bed drying, which provide similar advantages in drying. They can be advantageous for certain incorporated products, as the drying takes place under vacuum at low temperatures.

Another advantage of the fluidized-bed method is that it allows to perform both drying and coating with an additional substance in a single process step. The options in the coating process are diverse. For example, the granules can be dyed, or functional substances can be applied such as biopolymers (e.g., chitosan, etc.), synthetic polymers, active cosmetic or pharmaceutical agents, enzymes, proteins, and anticaking agents as well as grinding additives. A chemical modification of the surface of the granules in the fluidized bed is also possible. Coating in the fluidized bed makes the distribution of the coating across the surface and across the various particles very homogenous. Surprisingly, it has been found that the coated, fluidized-bed-dried molded bodies of the invention continue to exhibit a very good swelling behavior.

By selecting suitable drying methods, the pore structure and the density of the molded bodies of the invention can also be influenced significantly. In normal pressure drying at 60° C. in a recirculating-air oven, the sponge-like structure of the never-dried granules collapses completely, and a nearly transparent, compact, much smaller granule is created which, however, retains its ellipsoidal shape. Nevertheless, this effect of the collapse of the structure in the inner part of the granules is partly reversible, as the granules swell again in water. At normal pressure, fluidized-bed drying showed that in it the sponge structure of the never-dried granules could best be restored by subsequent swelling in water—as has already been set forth hereinabove.

However, the sponge structure was preserved a good deal better if the granules were made by shock freezing of the never-dried granules in liquid nitrogen and subsequent freeze drying. In this case, it was found that these dried granules were no longer transparent, but white. This indicates that the pore structure was preserved. However, the surface and shape of the granules changed significantly during drying. While the obtained product substantially maintained its ellipsoidal shape, indentations and craters similar to a lunar landscape had formed on the surface. This gave the granule a raisin-like appearance. Furthermore, the density of these granules was lower than that of water.

Supercritical $CO_2$ drying preceded by a solvent exchange was chosen as another type of drying used to dry the never-dried granules. Particularly, in this case, the water in the granules was exchanged for acetone, and then supercritical $CO_2$ drying was started. In this drying method, the original shape and porosity of the never-dried granules was preserved best. They had an ellipsoidal shape with a smooth surface. The fine pore structure became apparent from the white color of the granules. These granules also had a lower density than water.

The present invention also relates to the use of the molded bodies of the invention; due to their unique structure, they can be loaded with a wide variety of active agents.

According to the invention, the molded bodies can be used for the production of an active-agent-loaded carrier material, the molded body being soaked with a solution of the active agent and then washed and dried.

Furthermore, they can be used for the production of an active-agent-loaded carrier material having controlled release properties for cosmetic and pharmaceutical applications. To this end, it may be necessary to previously perform grinding of the molded bodies of the invention, with the controlled release properties remaining partly intact; in this connection, the following applications are particularly preferred: emulsions of natural substances, gel emulsions, personal care products for men, facial care products, sun protection productions, cosmetic serums, deodorizing applications, make-up foundations, and color cosmetics. The active agents may, for example, be enzymes and peptides for cosmetic and technical applications such as the coenzyme Q10.

According to the invention, the molded bodies can also be used as an abrasive material in cosmetic products such as peelings or exfoliator mixtures, the average size of the molded bodies being 150-800 μm, preferably 200-800 μm, more preferably 300-550 μm.

According to the invention, the molded bodies can also be used as optical effect granules in cosmetic products, preferably in shampoos and creams.

According to the invention, the molded bodies can, in both the never-dried and the dried states, also be used as a starting material for the production of spherical cellulosic powders having sensoric booster properties in oil/water emulsions. Preferably, the molded bodies are ground by means of various grinding methods to particle sizes of preferably $d_{50}=5$ μm. Then, they will be used for cosmetic and body care products. Their advantages are mainly that the final products exhibit lower stickiness and greasiness and enable enhanced absorption of lotions into the skin. Here, emulsions of natural substances, gel emulsions, personal care products for men, facial care products, sun protection productions, cosmetic serums, deodorizing applications, make-up foundations, and color cosmetics are particularly preferred.

In the technical field, the above-described molded bodies can, according to the invention, be used as a column material in chromatography, particularly in normal phase, reversed phase, ion exchange, affinity and size exclusion chromatography. For this purpose, the molded bodies can also be modified chemically, for example by acetylation, methoxylation, or similar methods.

Furthermore, the above-described molded bodies can, according to the invention, be used for the immobilization of enzymes or peptides in order to enhance their enzymatic activity or stability. In this connection, the use in the cosmetic and technical fields is particularly preferred. The above-described molded bodies can, according to the invention, also be used for the immobilization of cells of human, animal or plant origin (bacteria, fungi, tissues, algae, etc.).

The above-described molded bodies can be made handleable in various ways. According to the invention, a preferred variant is the incorporation into nonwovens. The nonwovens themselves can be produced according to the methods known from prior art such as carding, spunbonding, meltblowing, or air-laid methods. The incorporation can take place during the various stages of production of the nonwoven and/or on the finished nonwoven:

a. Prior to the formation of the nonwoven: In air-laid and wet-laid processes, the molded bodies of the invention can be mixed with the other starting materials, prior to the stage of nonwoven formation. In wet-laid processes, they can for example be dispersed in liquids or foam.

b. During the formation of the nonwoven: In extrusion processes such as meltblowing or spunbonding processes, the molded bodies of the invention can be added during or directly after the formation of filaments when the filament strands are deposited on the screen belt or the screen drum. The incorporation of the molded bodies can be performed, e.g., by spraying them into the filament curtain, or by spraying them on before or after the filament curtain is deposited on the screen belt or the screen drum.

c. After nonwoven formation, but prior to the consolidation stage.

d. After the consolidation stage (online), where the consolidation can be performed by means of known prior art methods, for example, by means of thermobonding, chemical crosslinking, air-through bonding, ultrasonic bonding, needlepunching, spunlacing, and also combinations of two or more of these methods.

e. On preconsolidated nonwovens, for example, prior to the application of a second nonwoven layer. Here, the preconsolidated nonwoven can, for example, also be fed from a roll in a batch process.

f. In methods that constitute a combination of the above-described variants a. to e.

In each of these methods, the molded bodies of the invention are fixed preferably by means of a binder, for example, by means of an adhesive.

These methods make it possible to produce a wide variety of layered structures from the molded bodies of the invention (A) and nonwovens (B): nonwovens coated with molded bodies on one side (A-B) or also on two sides (B-A-B), sandwich structures of two nonwovens with a molded body layer disposed in between (A-B-A), or also systems of multiple layers featuring alternating nonwoven and molded body layers (A-B-A-B, A-B-A-B-A, . . . ).

A variant that is also possible is the application of the molded bodies of the invention onto plastic films. Here, fixing of the molded bodies is preferably performed by means of adhesive, as well.

EXAMPLES

The following examples are used to illustrate and facilitate the understanding of the particles of the invention and of the ways to produce them. The invention itself, however, is not limited to these exemplary embodiments only.

Example 1—Production of Cellulose Beads

A standard lyocell spinning dope of the following composition was used as the starting material for the production of the cellulose beads: 13% by weight of cellulose (100% Saiccor), 75.3% by weight of NMMO, 11.7% by weight of water as well as traces of stabilizer. The spinning dope was kept at 120-125° C. and processed by means of an ECON EUP 50 underwater granulator. In this process, die plates with 12 holes and 4 cutter blades were used in each experiment. The temperature of the start-up valve and the die plate was controlled to a constant 120° C., that of the water tank to 20° C. Table 1 summarizes those parameters that were varied during experiments V1 to V6.

TABLE 1

|  | V1 | V2 | V3 | V4 | V5 | V6 |
| --- | --- | --- | --- | --- | --- | --- |
| Hole diameter [mm] | 1.0 | 1.5 | 1.5 | 1.5 | 1.5 | 1.5 |
| Cutter blade speed [rpm] | 4500 | 3000 | 3000 | 3000 | 3000 | 3000 |
| Precipitation bath temperature [° C.] | 30 | 50 | 50 | 50 | 50 | 10 |
| Concentration of NMMO in precipitation bath [% by weight] | 20 | 34.5 | 38.9 | 42 | 44.6 | 0 |
| Skin thickness [µm] - average value | 114.7 | 89.0 | 85.0 | 75.2 | 53.6 | 182.2 |
| Skin thickness [µm] - standard deviation | 20.1 | 14.7 | 4.2 | 7.7 | 8.0 | 35.3 |

The cellulose beads produced by means of the underwater granulator were precipitated in clean, deionized water (DI water) and subsequently subjected to washing in a column, using DI water heated to 80° C. For fine washing, caustic soda (pH 11) was used. After washing with caustic soda, the granules were washed neutral with DI water at a temperature of 80° C. and centrifuged to a residual moisture content of about 70% by weight.

The structure of the never-dried particles from experiments V1 to V6 was examined under an optical microscope (Zeiss Discovery.V12, Olympus DP71). It was found that all particles had a pronounced core/shell structure. FIG. 1 shows a particle from V6 as an example.

The thickness of the shell was measured using AnalySIS 5.0 software from Olympus, for which purpose five measurements were performed and averaged. The results are also summarized in Table 1. It was found that the shell thickness is clearly dependent on the regeneration conditions. The thickness of the outer layer decreases as the NMMO concentration in the precipitation bath increases and/or the temperature is increased.

Furthermore, it can be noticed that the outer skin is transparent, while the inner part of the granules is white. This clearly shows the different structuring of the material. The transparent layer is very dense, whereas the white inner part of the cellulose beads has a sponge-like structure. A detailed characterization of the core/shell structure can be found in connection with Example 5.

Example 2—Loading with Active Substance 40 ml of a solution of 5% by weight of paracetamol (Merck) in ethanol p.a., whose temperature was controlled to 30° C., were added to 20 g of never-dried cellulose beads V1 from Example 1 (68.3% by weight of residual moisture). This suspension was stirred at 100 rpm for 120 minutes. The loaded cellulose beads were filtered under suction and washed using 10 ml of deionized (DI) water and subsequently dried in the vacuum drying oven at 40° C., 150 mbar, for about 8 hours. The final weight of the dried cellulose beads was 5.6915 g. The amount of paracetamol the cellulose beads were loaded with was 8.48% by weight (weight increase).

The following materials were used as reference substances: Tencel® CP 4 (spherical cellulose powder, manufactured by Lenzing AG), Tencel® gel (cellulose suspension, Lenzing AG), and Vivapur 105 (MCC, manufactured by J. R. & Söhne). They were used to also prepare suspensions with paracetamol in ethanol, analogously to the cellulose beads of the invention, the cellulose-to-paracetamol ratio being kept constant in each case. However, the reference materials were not dried in the vacuum drying oven, as this would have led to the formation of lumps because of the fine particles, but by means of a Büchi B290 spray dryer. Table 2 summarizes the properties of the loaded particles.

TABLE 2

| Material | Beads V1 | Tencel® CP4 | Tencel® gel | Vivapur 105 |
|---|---|---|---|---|
| d50 [μm] | 1260 | 7.5 | 6.3 | 10.5 |
| Loading [% by weight] | 8.48 | 5.17 | 10.05 | 5.23 |

Example 3—Release Experiments

Figure 2:
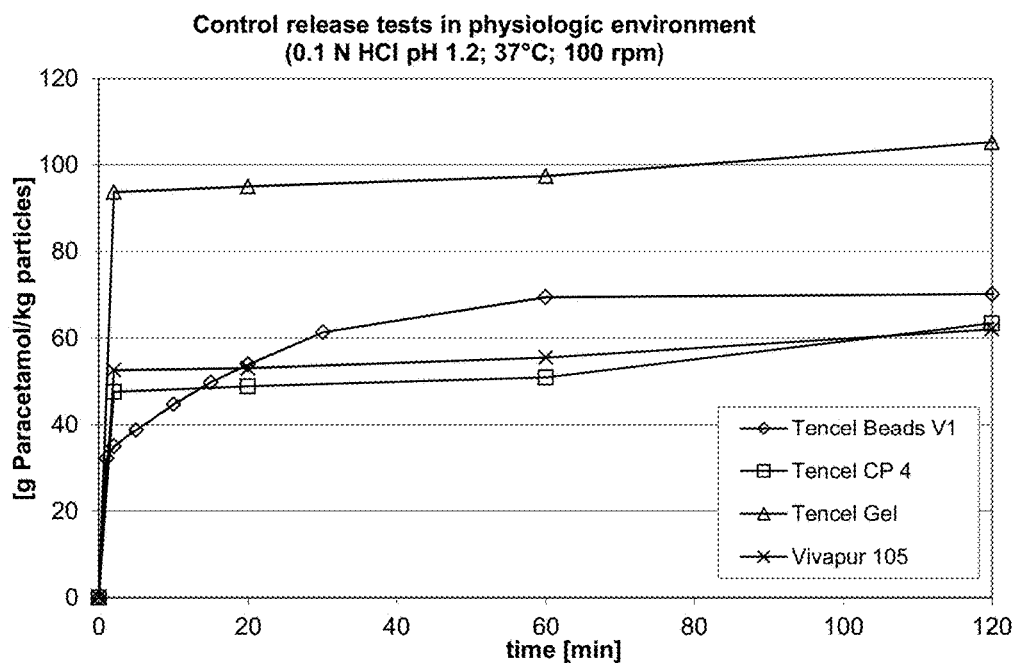
FIG. 2 is a release curve comparing the rate of release of paracetamol from exemplary cellulose beads made in accordance with the present invention to reference cellulose beads.

The rate of release of paracetamol from the loaded particles produced in Example 2 was determined according to the method described hereinafter. For this purpose, 100 mg of the particles were introduced into 500 ml of aqueous hydrochloric acid (0.1 M; pH 1.2) and stirred at 100 rpm at 37° C. (agitating device: Erweka Dissolution Tester DT 820). Samples were taken at regular intervals, and the absorbance at 243 nm was measured (Perkin Elmer Lambda 950 UV/VIS spectrometer) in comparison with a reference (pure aqueous hydrochloric acid). FIG. 2 shows the release curves for the various particles.

It becomes apparent that the cellulose beads of the invention have a significant retarding effect on paracetamol as the active agent. Compared to powdery particles loaded by spray drying, this retarding effect is much stronger. In the particles made from the cellulose gel, the highest degree of loading can be obtained due to the even more open structure. However, also in this case, the release takes place abruptly; only the cellulose beads of the invention exhibit slow release properties because of their inner structure.

Example 4—Drying (Including Coating)

The never-dried cellulose beads V1 from Example 1 (residual moisture: 63.83%) were subjected to various drying methods in order to study their impact on the structure of the dried particles:
Drying oven at 60° C.
Fluidized-bed drying (in a DMR WFP-8 fluidized-bed dryer) at 100° C.
Drying with supercritical CO2 (Natex 51 laboratory system)—after solvent exchange to acetone ("sc-$CO_2$ drying")
Freeze drying (Labconco Freezone 2.5 liters, vacuum 0 mbar) after shock freezing in liquid $N_2$ In the fluidized-bed drying procedures, additional coating experiments were conducted. For this purpose, suitable aqueous dye solutions (Waco blue, Waco pink, SepiCoat 3213 Yellow+Sepifilm Gloss, Sepicoat 3404 Green+Sepifilm Gloss, Sepicoat 5901 Brown+Sepifilm Gloss) were injected into the fluidized-bed dryer. All obtained particles exhibited homogenous coloring at their surfaces.

Figure 3:
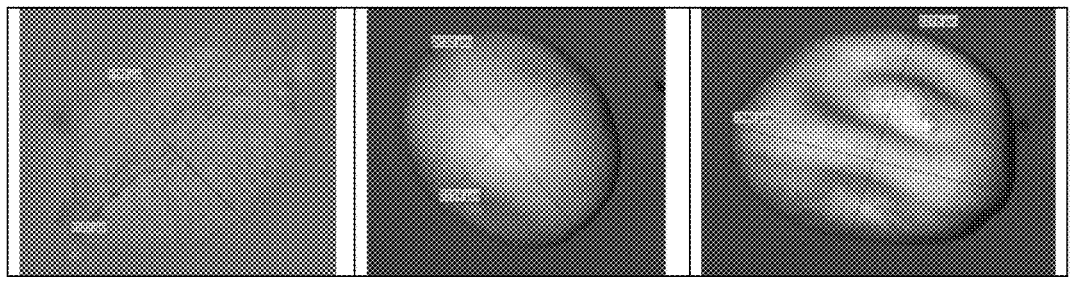
FIG. 3 depicts the structures of cellulose beads made in accordance with the present invention after employing various drying methods including: (left) being dried in an oven, (middle) sc-$CO_2$ drying, and (right) freeze drying.
Figure 4:
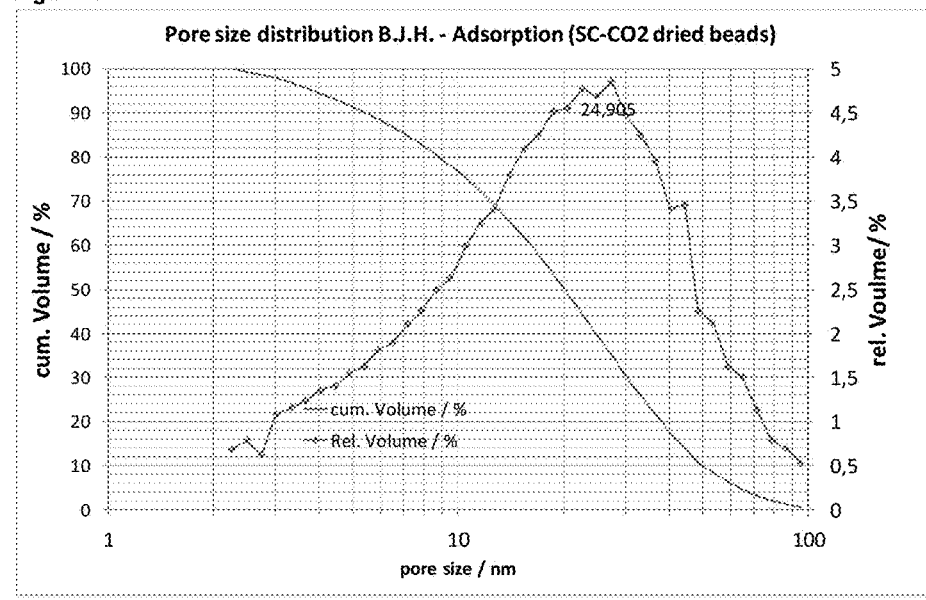
FIG. 4 depicts a pore size distribution plot of exemplary sc-$CO_2$-dried cellulose beads made in accordance with the present invention.

In all drying methods, shrinkage of the particles was observed. Thus, after drying in the drying oven, the cellulose beads, for example, had a bulk density of 0.74 g/ml, while the never-dried cellulose beads still had a bulk density of 0.72 g/ml. The increase in bulk density directly implies a decrease in particle size. FIG. 3 shows typical structures obtained from the various drying methods:
Left: drying oven—transparent to slightly opaque cellulose bead having a rough surface
Center: sc-CO2 drying—white cellulose bead having a smooth surface
Right: freeze drying—white cellulose bead having a smooth, but deformed surface However, the drying method has an impact not only on the outer appearance of the particles, but also on their inner structure. To this end, the BET surface of the particles was determined by means of $N_2$ adsorption (BELsorp mini II measuring device). For the cellulose beads dried in the drying oven, no BET surface was determined by means of this measurement, which means that the inner pore structure has collapsed entirely. For the sc-$CO_2$-dried sample, a BET surface $a_{BET}=174$ m$^2$/g was measured, which suggests that the pore structure present in the never-dried state was largely preserved. Yielding $a_{BET}=45$ m$^2$/g, the freeze-dried sample was between the other two methods as expected. Furthermore, FIG. 4 shows the pore size distribution of the sc-$CO_2$-dried cellulose beads by means of a B.J.H. plot (calculated from the $N_2$ adsorption/desorption) which is focused on the area around 25 nm.

Furthermore, it was demonstrated by heliumpyknometry (Pycnomatic ATC by ThermoFisher/Porotec) that the sc-$CO_2$-dried cellulose beads have an open-pore structure, whereas the freeze-dried cellulose beads have a closed-pore structure.

Example 5—Characterization of the Core/Shell Structure $C^{13}$ CP-MAS-NMR measurements (Bruker Avance DPX 300 NMR spectrometer, 7.05T Ultrashield (SB) magnetic field strength, 2 if channels, 100/300 W $^1$H/BB amplifier, 4 mm $^1$H/BB solid state CP-MAS probe) were conducted on the never-dried samples V4 and V6 of Example 1 which showed a markedly different thickness of the shell (75 μm and 182 μm, respectively). From these measurements, the inner-crystalline (IC), surface-crystalline (SC) and disordered (DIS) fractions were determined according to the method described in "G. Zuckerstätter et al., Novel insight into cellulose supramolecular structure through $^{13}$C CP-MAS NMR spectroscopy and paramagnetic relaxation enhancement, Carbohydrate Polymers 93 (2013), pp. 122-128".

Figure 5:
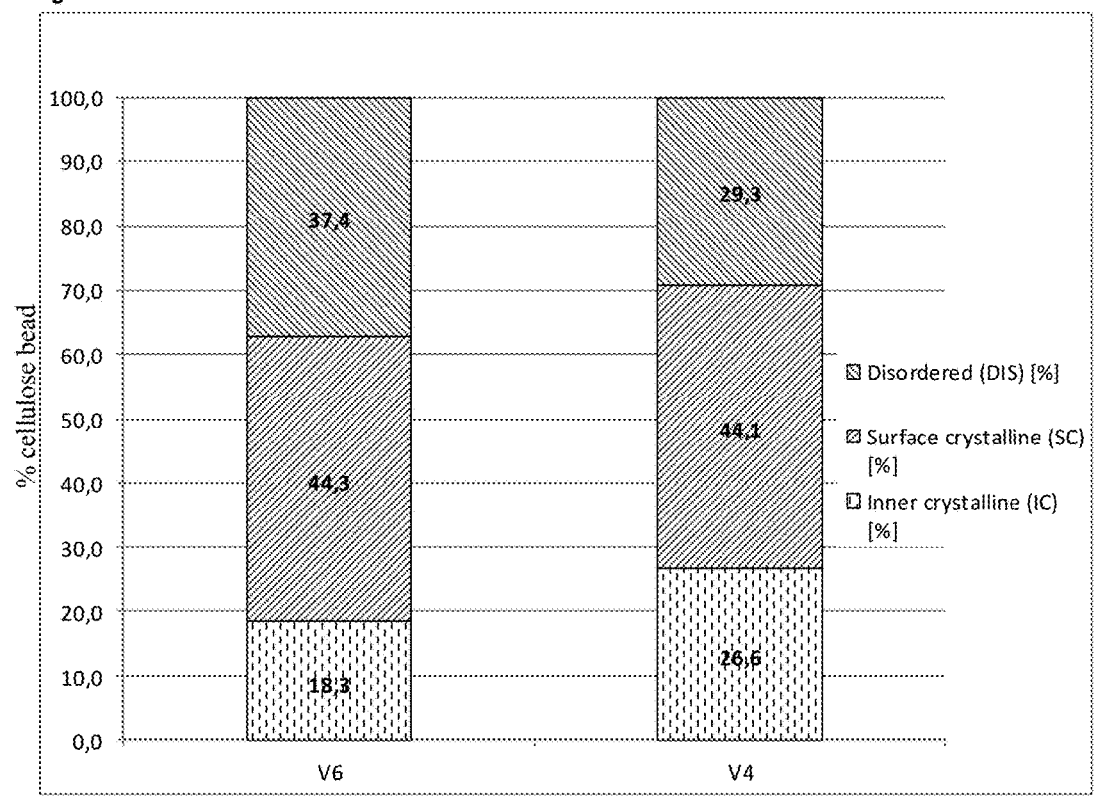
FIG. 5 depicts a graph plotting NMR measurements for cellulose beads made in accordance with the present invention.

From the results illustrated in FIG. 5, it can be recognized clearly that a reduction of the precipitation bath temperature from 50° C. (V4) to 10° C. (V6) and a reduction of the NMMO concentration in the precipitation bath from 44.6% by weight of NMMO (in V4) to 0% by weight of NMMO (in V6) causes the disordered regions to increase from 29.3% to 37.4%. This causes the inner-crystalline portion to be reduced accordingly, as the surface-crystalline portion remains constant. Therefore, it can be said that the thickness of the outer skin is correlated with the disordered portions, and one can clearly identify the outer skin as amorphous part of the granules. Computer tomography measurements can be used to determine clearly that this amorphous outer skin consists of a material of greater density than the core.

These x-ray computer tomography measurements were conducted with a GE Phoenix/x-ray Nanotom device and a voxel size of 4.5 μm, the measuring period was 121 min, and a total of 1700 projections were recorded. The measurements were conducted on whole (and not on comminuted) cellulose beads: the freeze-dried and sc-$CO_2$-dried cellulose beads of Example 4, as well as commercially available compact cellulose granules (Sprayspheres-SE white, Umang). Conducting a useful measurement on the moist cellulose beads was not possible. Using VG Studio MAX 2.2 software, (virtual) cuts were made through the particles and evaluated in terms of the grey scales (correspond to the scatter density). In this process, a relative density of 0% was defined for air (gaps between particles) and a relative density of 100% was defined for compact cellulose (Sprayspheres). Table 3 shows the values obtained for the dried Tencel® beads.

TABLE 3

| | Relative density of shell | Relative density of core |
|---|---|---|
| Tencel(R) beads, freeze-dried | 71.8% | 54.4% |
| Tencel(R) beads, sc-dried | 72.8% | 26.0%-42.2% |
| Sprayspheres SE | 100% (homogenous, reference) | |

Example 6—Swelling Behavior of Dried Cellulose Beads

The fluidized-bed-dried (uncoated) cellulose beads of Example 4 were examined for their swelling behavior in water. Again, commercially available cellulose granules (Sprayspheres-SE White, Umang) produced by spray granulation were used as a reference material. 10 g of particles each were introduced in 100 ml of DI water and allowed to swell without any further movement (agitation or the like) until an equilibrium was reached. Table 4 summarizes the results of these experiments.

TABLE 4

| | Starting moisture [% by weight] | Size d50 [μm] | Swelling duration [min] | Bulk swelling [% by volume] | Moisture absorption [% by weight] |
|---|---|---|---|---|---|
| Tencel beads | 9.9 | 1207 | 180 | 170 | 99 |
| Sprayspheres | 8.7 | 734 | 40 | 90 | 63 |

It has been found that the Tencel beads of the invention exhibit a significantly better swelling behavior than comparable commercially available cellulose particles. This, in turn, can be attributed to the inner structure that has already been described in the preceding examples.

Example 7—Variation of the Strength of Particles Caused by Enzymatic and Chemical Treatment The never-dried cellulose beads V1 of Example 1 were subjected to both an enzymatic and an oxidative treatment, for which the following parameters were used:

In a buffer solution (pH 4), a solution of the enzymes Celluclast 1.5 L and Econase HC 400 (Novozyme) was prepared in a ratio of 2:1. Another enzyme treatment option results from the use of Novozyme FiberCare R or FiberCare D in a pH 6.5 buffer solution. In each case, the cellulose beads were introduced into a buffer solution (40° C.) and subsequently the respective enzyme solution was added in a dose corresponding to 1 ml per gram of dry cellulose beads. The reaction time was 10 min and 60 min, whereupon the reaction was stopped through enzyme deactivation, and the cellulose beads were rinsed with DE water several times.

Oxidation occurred via the known TEMPO reaction, the reaction time in this case being 4 h at 80° C. After stopping the reaction by adding EtOH and thorough washing of the cellulose beads with DI water, a subsequent oxidation was still performed for 48 h in 0.1 M Na-acetate buffer (pH=4.5). After the reaction, the particles were filtered under suction, washed thoroughly, and stored in a refrigerator.

The strength of the cellulose beads was examined by using various plungers of differing weight that were placed on top of a defined quantity of cellulose beads. Furthermore, microscopic images of the particles were recorded again in order to analyze changes in morphology.

Enzymatically treated never-dried cellulose beads (reaction times: 10 min and 60 min) are crushed by the net weight of a 100 g plunger. Untreated cellulose beads are only deformed reversibly by the plunger's own weight. Untreated cellulose beads (blank value) are irreversibly deformed only by a plunger having a net weight from 3 kg onward and crushed only from 5 kg onward. The crushed enzymatically treated cellulose beads have a hydrogel-like consistency and are neither sticky, nor greasy.

Similar to the enzymatic treatment, the structural integrity of the granules was also reduced significantly by the TEMPO oxidation. Therefore, these granules can already be deformed irreversibly with cracking by a 1 kg plunger. From a 2 kg plunger onward, severe cracking is obtained, and a 5 kg plunger already crushes the cellulose beads entirely.

Figure 6:
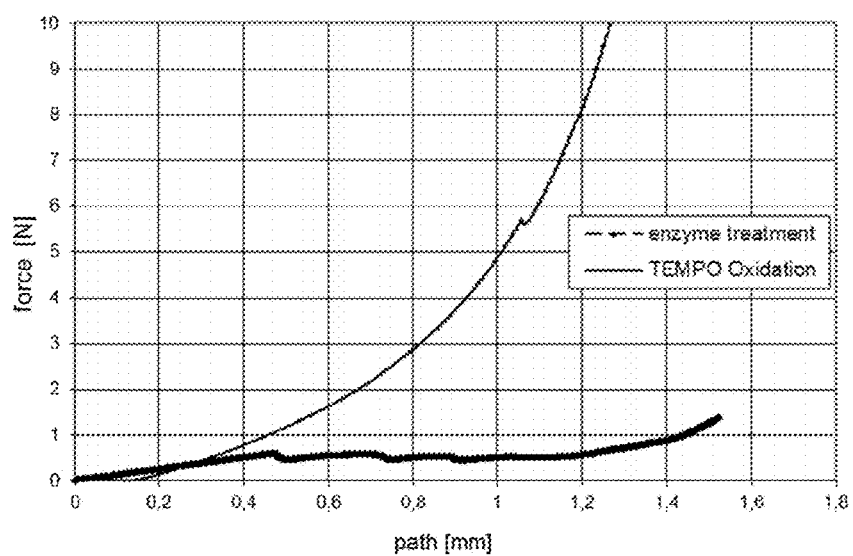
FIG. 6 depicts deformation curves for cellulose beads made in accordance with the present invention which have been subjected to an enzymatic treatment or an oxidative treatment.

Apart from these simple experiments used to determine the hardness, a Shimadzu EZ Test X hardness tester was used to also determine the microhardness of select samples. Testing was conducted with a 10 mm plunger, and the deformation against the applied force was recorded. FIG. 6 shows the deformation curves for enzyme-treated and TEMPO-oxidized samples.

In the enzymatically treated samples, a dramatic change of the morphology was observed. Not only was the surface smoothed, but the core/shell structure disappeared as well. This shows that both the dense outer skin and the inner part of the cellulose beads are accessible to the enzymes and are decomposed. There was no longer any difference to be detected between the outer skin and the inner part of the cellulose beads; both are parts of a hydrogel.

Figure 7:
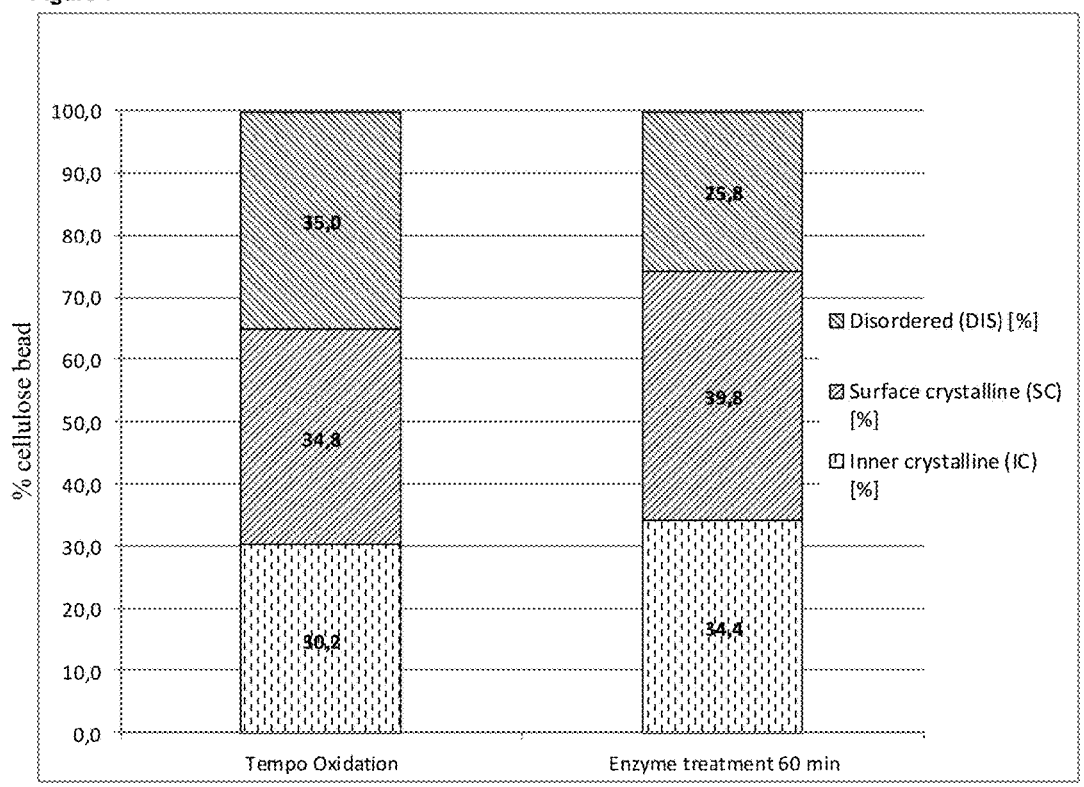
FIG. 7 a graph plotting NMR measurements for cellulose beads made in accordance with the present invention which have been subjected to an enzymatic treatment or an oxidative treatment.

These morphological changes upon TEMPO oxidation and enzyme treatment, respectively, can also be confirmed in NMR studies (see FIG. 7) as previously described in Example 5. Hence, the disordered cellulose fraction decreases upon enzyme treatment, and the inner-crystalline fraction is consequently increased. Upon TEMPO oxidation, the surface-crystalline fraction decreases sharply, as a result of which the inner-crystalline fraction increases.

Example 8—Incorporation of Inorganic Pigments

Figure 8:
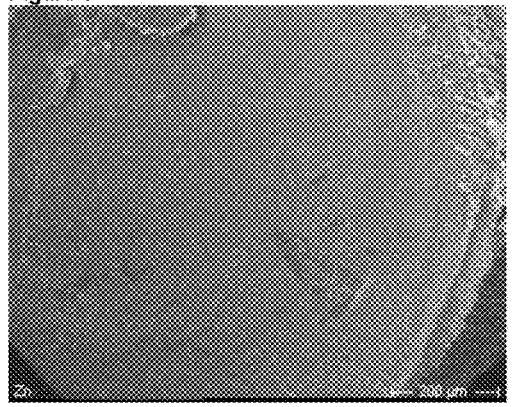
FIG. 8 depicts a scanning electron microscope image of a cellulose bead comprising an organic pigment made in accordance with the present invention.

A suspension of 33% by weight of ZnO (Type Pharma 4, $d_{50}$=1.2 µm) in 60% by weight of aqueous NMMO was used to produce lyocell spinning dope. The finished spinning dope consisted of 12.2% by weight of pulp (Bacell type), 73.9% by weight of NMMO, 11.5% by weight of water, 2.4% by weight of ZnO, and traces of stabilizer. Then, cellulose beads as described in Example 1, V1, were produced from this spinning dope. The outer appearance of the cellulose beads matched that of the cellulose beads without added ZnO. The ZnO content of the particles was determined to be 16.7% by weight (ashing of the granules at 850° C., and gravimetric evaluation of the residue versus the blank value of a granule without ZnO), and the distribution was measured by means of a SEM (Hitachi S-4000 Field Emission SEM) with integrated EDX (Oxford EDX Detector). FIG. 8 shows the very uniform Zn distribution in such a bisected Tencel bead.

What is claimed is:

1. A three-dimensional cellulosic molded body comprising an optically detectable core/shell structure, the shell having a higher density and a lower crystallinity than the core, the core having a sponge-like structure, wherein the shell has a relative density from 65% to 85% and the core has a relative density from 20% to 60%—related to compact cellulose, wherein the shell has a thickness between 50 µm and 200 µm, and wherein a ratio of the shell thickness to a total diameter of the molded body is between 1:5 and 1:50.

2. The molded body as claimed in claim 1, wherein a ratio of the semiaxes of a ellipsoidal molded body does not exceed 3:1.

3. The molded body as claimed in claim 1, wherein a never-dried variant of cellulose beads has a moisture content from 25 to 300% by weight, related to a cellulose quantity.

4. A method for producing a three-dimensional cellulosic molded body of claim 1, having an optically detectable core/shell structure, comprising the following production steps:
   a. dissolution of the cellulose according to a lyocell process in order to obtain a solution with 10 to 15% by weight of cellulose;
   b. extrusion of the cellulose solution obtained in step a. without air gap directly into a precipitation bath;
   c. regeneration process, where, when the cellulose solution enters the precipitation bath, the difference between the NMMO concentrations of the cellulose solution and the precipitation bath is to be 15-78% by weight, and the difference between the temperatures of the cellulose solution and the precipitation bath is to be 50-120 K;
   d. washing process according to the percolation principle, comprising at least one alkaline washing step, preferably at pH 9-13; and
   e. optionally a drying process that does not abrasively damage the outer skin of the molded bodies.

5. The method as claimed in claim 4, wherein an enzyme treatment is performed between step d and step e.

6. The method as claimed in claim 5, wherein the enzyme treatment includes one or more enzymes selected from the group consisting of exo- and endo-1,4-b-glucanases glucosidases, and xylanases.

7. The molded body of claim 1, wherein an average size of the molded body is 150-800 µm.

8. The molded body of claim 1, wherein the molded body is a column material for chromatography, wherein the chromatography is selected from the group consisting of normal phase, reversed phase, ion exchange, affinity and size exclusion chromatography.

9. The molded body as claimed in claim 1, wherein the molded body comprises additive substances incorporated during production and wherein the additive substances are selected from the group consisting of ZnO, $TiO_2$, $CaCO_3$, kaolin, $Fe_2O_3$, plastic-based color pigments, activated carbon, superabsorbent materials, phase-change materials, flame retardants, biocides, chitosan, polymers and biopolymers.

10. The method of claim 4, further comprising soaking the molded body in a solution of an active agent.

11. The method of claim 10, wherein the active agent is selected from the group consisting of a cosmetic agent, a pharmaceutical agent, an enzyme, a peptide and combinations thereof.

12. The method of claim 10, wherein the molded body has controlled release properties.

13. The molded body of claim 1, further comprising an active agent.

14. The molded body of claim 13, wherein the active agent is selected from the group consisting of a cosmetic agent, a pharmaceutical agent, an enzyme, a peptide and combinations thereof.

15. The molded body of claim 13, wherein the molded body has controlled release properties.

16. The method as claimed in claim 4, wherein the drying process is selected from the group consisting of normal-pressure drying, air stream drying, belt drying, fluidized-bed drying, freeze drying, and supercritical CO2 drying.

17. The method according to claim 4, wherein the cellulose solution and the precipitation bath is 15-78% by weight.

18. The method according to claim 17, wherein the cellulose solution and the precipitation bath is preferably 40-70% by weight.

19. The method according to claim 4, wherein the difference between the temperatures of the cellulose solution and the precipitation bath is 70-120 K.

20. The method according to claim 19, wherein the difference between the temperatures of the cellulose solution and the precipitation bath is 80-120 K.

21. The method according to claim 4, wherein the washing process mentioned in d) is performed in several stages and in a countercurrent configuration and comprises at least one alkaline step.

22. A cosmetic product comprising the molded body of claim 1, wherein said cosmetic product is selected from the group consisting of shampoo, cream, peelings, exfoliators and combinations thereof.

23. The cosmetic product of claim 22, wherein an average size of the molded body is 150-800 μm.

24. The cosmetic product of claim 23, wherein the average size of the molded body is 200-800 μm.

25. The cosmetic product of claim 24, wherein the average size of the molded body is 300-550 μm.

* * * * *